United States Patent
Karnes et al.

(10) Patent No.: US 9,089,433 B2
(45) Date of Patent: Jul. 28, 2015

(54) CANINE ELBOW REPAIR AND INSTRUMENTATION

(71) Applicant: Arthrex, Inc., Naples, FL (US)

(72) Inventors: G. Joshua Karnes, Estero, FL (US); James L. Cook, Columbia, MO (US); Kurt S. Schulz, Williston, VT (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 13/911,150

(22) Filed: Jun. 6, 2013

(65) Prior Publication Data

US 2013/0268082 A1    Oct. 10, 2013

Related U.S. Application Data

(62) Division of application No. 12/395,992, filed on Mar. 2, 2009, now Pat. No. 8,475,534.

(60) Provisional application No. 61/032,893, filed on Feb. 29, 2008, provisional application No. 61/048,451, filed on Apr. 28, 2008.

(51) Int. Cl.
| | |
|---|---|
| *A61F 2/38* | (2006.01) |
| *A61B 17/16* | (2006.01) |
| *A61B 17/17* | (2006.01) |
| *A61B 17/92* | (2006.01) |
| *A61B 19/00* | (2006.01) |
| *A61F 2/30* | (2006.01) |

(52) U.S. Cl.
CPC ........... *A61F 2/3804* (2013.01); *A61B 17/1615* (2013.01); *A61B 17/1659* (2013.01); *A61B 17/1662* (2013.01); *A61B 17/1739* (2013.01); *A61B 17/92* (2013.01); *A61B 17/1684* (2013.01); *A61B 2017/1778* (2013.01); *A61B 2019/304* (2013.01); *A61F 2002/30703* (2013.01)

(58) Field of Classification Search
USPC ..................... 623/20.11–20.36; 606/86 R–89
See application file for complete search history.

(56) References Cited

U.S. PATENT DOCUMENTS

| | | |
|---|---|---|
| 5,879,389 A | 3/1999 | Koshino |
| 2002/0183760 A1 | 12/2002 | McGovern et al. |
| 2006/0009853 A1 | 1/2006 | Justin et al. |
| 2007/0073408 A1* | 3/2007 | Acker et al. ............... 623/20.11 |
| 2007/0233128 A1 | 10/2007 | Schmieding et al. |
| 2008/0275512 A1 | 11/2008 | Albertorio et al. |
| 2009/0275950 A1 | 11/2009 | Sterrett |

FOREIGN PATENT DOCUMENTS

EP    1 987 786    11/2008

* cited by examiner

*Primary Examiner* — Andrew Yang
*Assistant Examiner* — Olivia C Chang
(74) *Attorney, Agent, or Firm* — Dickstein Shapiro LLP

(57) ABSTRACT

Instrumentation and assembly for arthroscopic elbow surgery which includes a humeral component. The humeral component is installed in a trough formed in the humeral condyle. The trough may be formed by using a plurality of drill pins and a plurality of corresponding cutters (and optionally a template). The two drill pins are passed through the template and drilled into the humerus, and cutters are advanced over the corresponding drill pins to form the trough. The humeral component may be employed in conjunction with an ulnar implant.

4 Claims, 17 Drawing Sheets

CANINE ELBOW REPAIR AND INSTRUMENTATION

CROSS-REFERENCE TO RELATED APPLICATIONS

This is a divisional of U.S. application Ser. No. 12/395,992, filed Mar. 2, 2009, which claims the benefit of U.S. Provisional Application No. 61/032,893, filed Feb. 29, 2008, and U.S. Provisional Application No. 61/048,451, filed Apr. 28, 2008, the entire disclosures of which are incorporated by reference herein.

FIELD OF THE INVENTION

The present invention relates to open and arthroscopic surgical methods and instruments and, more specifically, to elbow reconstruction in mammals, in particular, canines.

BACKGROUND OF THE INVENTION

Various improvements in repairing damage to elbow joints have been made over the years, some of the major advances involving endoscopic techniques and arthroscopic procedures. Arthroscopic surgery is particularly useful in excising or repairing damaged elbow cartilage.

Ligament repairs in mammals, particularly canine repairs, are becoming increasingly important. In the United States alone, the number of canine surgeries per year is estimated to be between about 50,000 to about 100,000.

An improved canine elbow reconstruction technique is needed which provides increased fixation strength and optimal tension of the repair.

SUMMARY OF THE INVENTION

The present invention provides apparatus, instrumentation and methods for reconstructive elbow surgery, with particular application to canine elbow surgery, which fulfill the above-noted need.

The present invention provides humeral and ulnar components for reconstructive elbow surgery. The humeral component may have an outer surface shaped in the form of a humeral condyle and, optionally, with two projections extending from the opposite surface for securing the component in the humerus. The humeral component may be employed with an ulnar implant which may be provided with different contours (for example, flat, concave, or angled).

The present invention also provides instrumentation (humeral guide systems and drills for the formation of the ulnar tunnels or sockets) and methods for the formation of a humeral trough (to accept a humeral implant) and of an ulnar trough (to accept an ulnar implant). An assembly for forming a humeral trough includes a template (broach), a plurality of drill pins and a plurality of corresponding cutters. The assembly is employed to create a humeral trough in a humeral condyle. A cutter, for example, a retrodrill cutter or a flip retrograde cutter, is employed to create at least one socket from outside in, before the formation of the humeral trough.

The present invention also provides a method of forming a humeral trough to accept a humeral implant. A template or broach is aligned with the curvature of the humeral condyle. Drill pins are inserted through the template and cutters are then inserted over the corresponding drill pins. The cutters are then used to drill into the humeral condyle to form a trough in the humerus. In lieu of using the template assembly, two initial sockets may be formed close to each other to allow overlap of the socket contours and to form a humeral trough having a snowman shape configuration. A humeral implant is subsequently mounted and secured to match the contour of the snowman-shaped humeral trough.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

Figure 1:
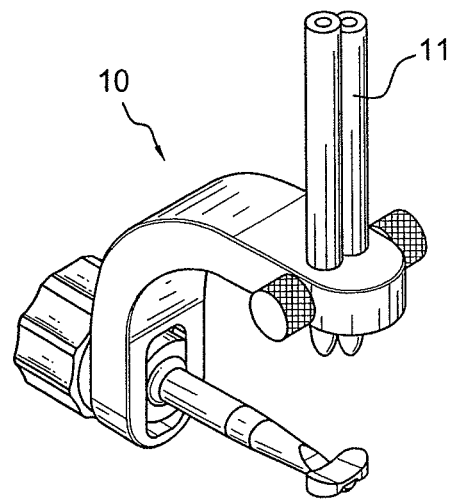
FIG. 1 illustrates a perspective view of a C-Ring assembly employed in the method of canine elbow reconstruction of the present invention.

The following description is provided to enable any person skilled in the art to make and use the invention and sets forth the best modes contemplated by the inventors of carrying out their invention. Various modifications, however, will remain readily apparent to those skilled in the art.

The present invention provides apparatus and methods for reconstructive elbow surgery, with particular application to canine elbow surgery.

The present invention provides a humeral component having an outer surface shaped in the form of a humeral condyle and, optionally, with two projections extending from the opposite surface for securing the component in the humerus. The humeral component is preferably made of cobalt-chrome alloy. The humeral component may be employed with an ulnar implant which may be provided with different contours (for example, flat, concave, or angled).

The present invention also provides an assembly for forming a humeral trough including a template or broach, a plurality of drill pins and a plurality of corresponding cutters. The assembly is employed to create a humeral trough in a humeral condyle. A cutter, for example, a retrodrill cutter or a flip retrograde cutter is employed to create at least one socket from outside in, before or after the formation of the humeral trough.

The present invention also provides a method of forming a humeral trough to accept a humeral implant. A template or broach is aligned with the curvature of the humeral condyle. Drill pins are inserted through the template and cutters are inserted over the corresponding drill pins. The cutters are then used to drill into the humeral condyle to form a trough in the humerus.

The present invention also provides a method of arthroscopically preparing the humerus to accept a humeral implant for repairing the articulating surface of the humerus. The method includes forming a humeral socket and creating a trough in the humeral condyle, as described above. The humeral implant is then mounted and secured in the humeral trough.

In lieu of using the template assembly, two initial sockets may be formed close to each other to allow overlap of the socket contours and to form a humeral trough having a snowman shape configuration. A humeral implant is subsequently mounted and secured to match the contour of the snowman-shaped humeral trough.

In an alternative embodiment, the present invention provides a humeral component having an outer surface with a simple or compound curvature that follows the anatomical geometry of the proximal humerus. The humeral component may be employed with an ulnar implant that may be provided with different contours (such as flat, concave, or angled, for example). The present invention also provides instrumentation (such as a humeral guide system, and/or drills for the formation of the ulnar tunnels or sockets) and methods for the formation of a humeral trough (to accept a humeral implant) and of an ulnar trough (to accept an ulnar implant).

As described in more detail below, an exemplary method for elbow reconstruction in mammals begins by exploring the elbow joint, and then debriding the damaged elbow ligament and meniscus. The MCL is released to allow a C-Ring (for example, a double barrel C-Ring) to be introduced into the joint capsule. The drill sleeve of the C-Ring assembly is adjusted to be flush with the bone. Using a drill, pilot holes are first formed in humerus and, once the C-Ring is removed, two sockets of about 6 mm depth are created using a cutting instrument (for example, a flip retrograde cutter). A template (broach) is then introduced (with thread guide posts) over the two sockets. Using a slap hammer, for example, the template is advanced into the sockets until the apex of humerus is flush with the top surface of the template. The broached contour (trough) creates a hard stop for insertion of the implant. Once the template assembly is removed, the humeral implant is introduced over the broached contour (trough) created by the removal of the template and then back filled with cement.

Alternatively, the two initial sockets may be formed close to each other to allow overlap of the socket contours and to form a humeral trough having a snowman shape configuration. A humeral implant is subsequently mounted and secured to match the contour of the snowman-shaped humeral trough.

Figure 2:
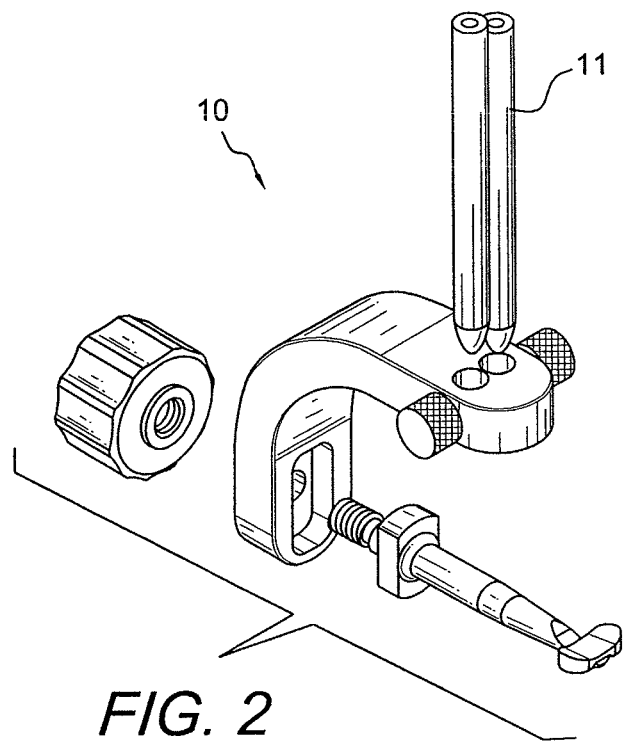
FIG. 2 illustrates an expanded view of the elements of the C-Ring assembly of FIG. 1.
Figure 3:
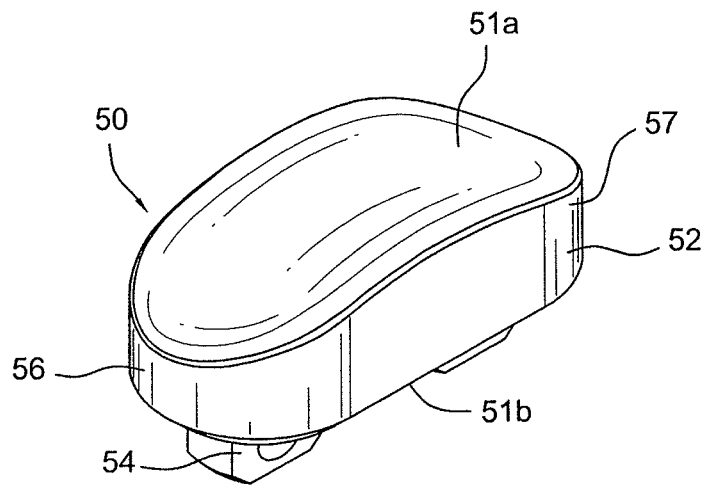
FIG. 3 illustrates a perspective view of a humeral implant according to a first embodiment and used in the method of canine elbow reconstruction of the present invention.
Figure 4:
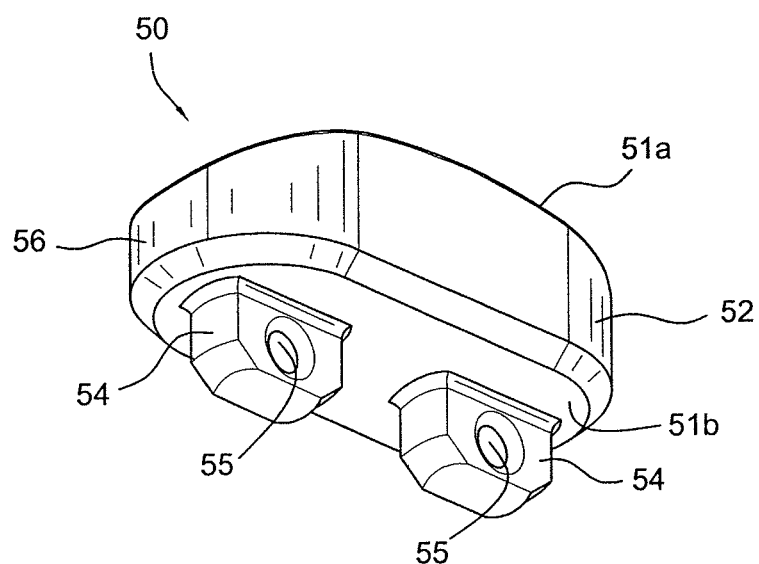
FIG. 4 illustrates another perspective view of the humeral implant of FIG. 3.
Figure 13:
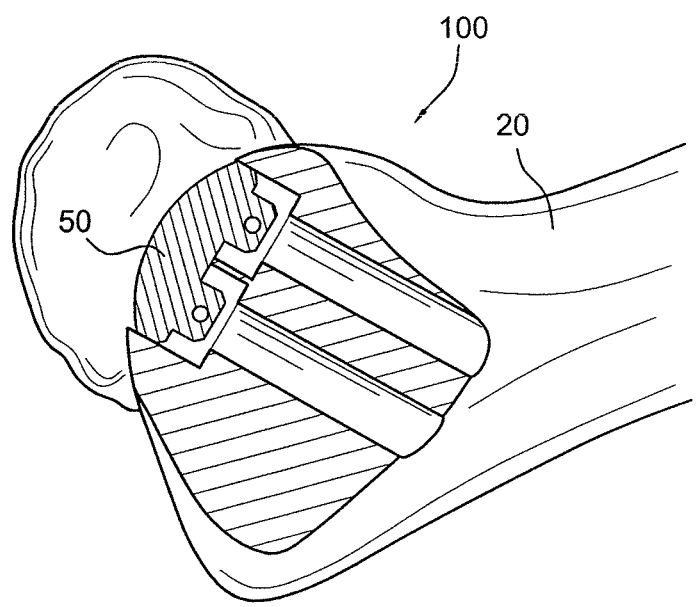
FIG. 13 illustrates a schematic view of the proximal end of the humerus of FIG. 8 and at a stage of reconstruction subsequent to that shown in FIG. 12.
Figure 14:
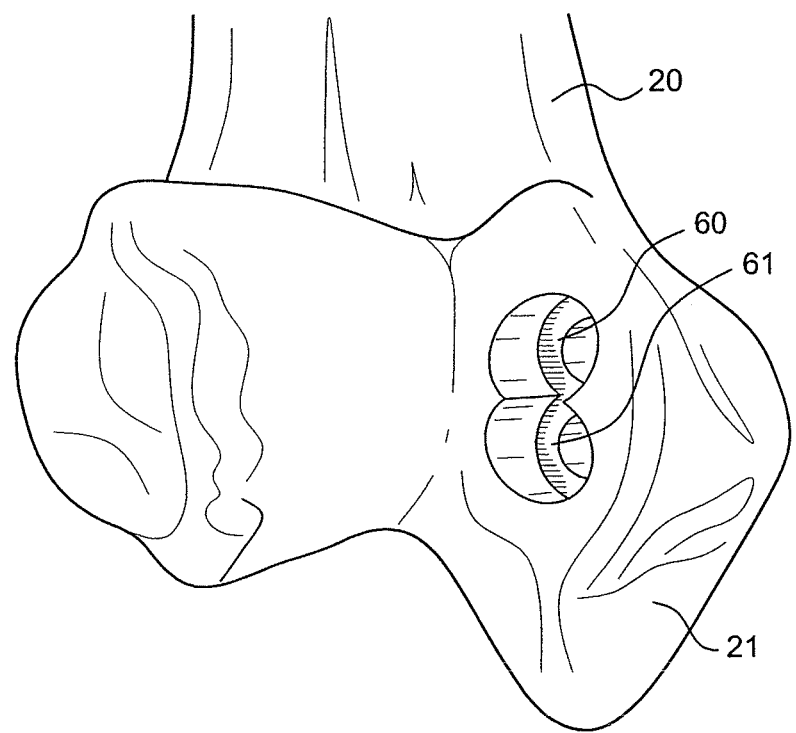
FIG. 14 illustrates a schematic view of a proximal end of a humerus of a canine elbow undergoing a method of elbow reconstruction according to a second embodiment of the present invention.
Figure 15:
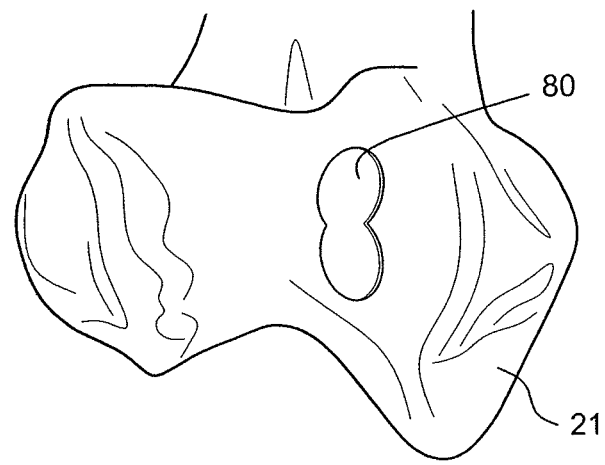
FIG. 15 illustrates a schematic view of the proximal end of the humerus of FIG. 14 and at a stage of reconstruction subsequent to that shown in FIG. 14.
Figure 16:
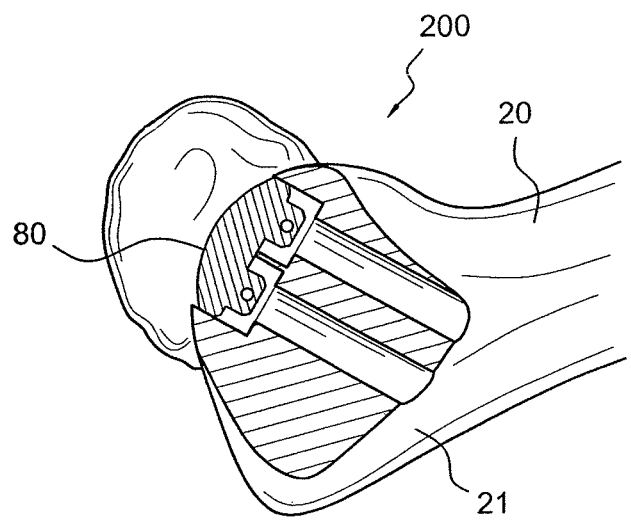
FIG. 16 illustrates a schematic view of the proximal end of the humerus of FIG. 14 and at a stage of reconstruction subsequent to that shown in FIG. 15.
Figure 18:
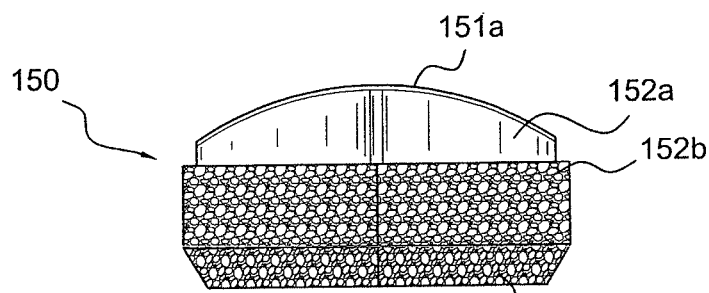
FIG. 18 illustrates a side view of a humeral implant according to a third embodiment and used in a method of canine elbow reconstruction of the present invention.
Figure 19:
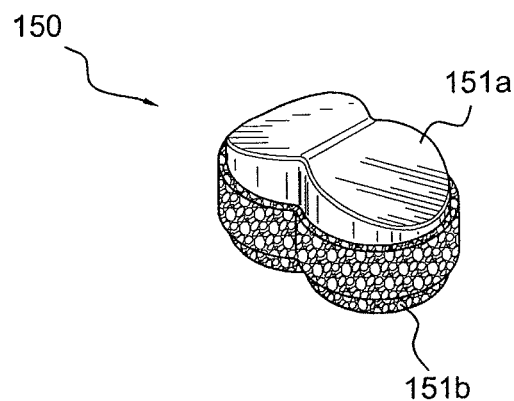
FIG. 19 illustrates a perspective view of the humeral implant of FIG. 18.
Figure 20:
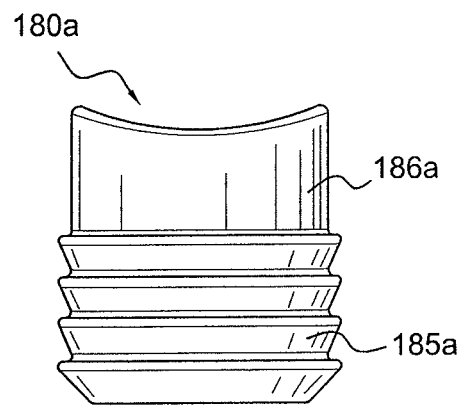
FIG. 20 illustrates a side view of an ulnar implant according to a first embodiment and used in conjunction with the humeral implant of FIG. 18.
Figure 21:
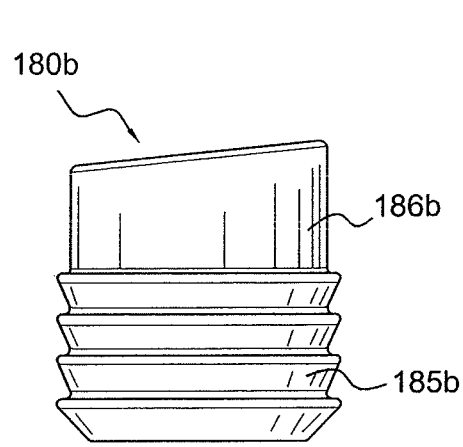
FIG. 21 illustrates a side view of an ulnar implant according to a second embodiment and used in conjunction with the humeral implant of FIG. 18.
Figure 22:
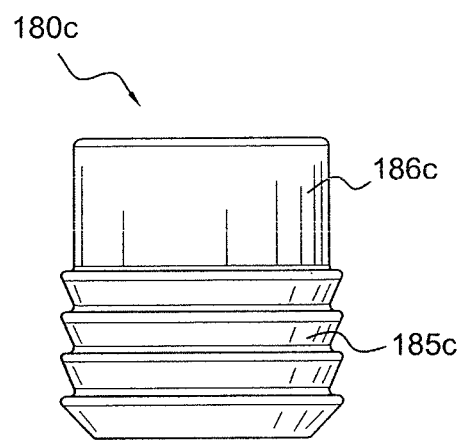
FIG. 22 illustrates a side view of an ulnar implant according to a third embodiment and used in conjunction with the humeral implant of FIG. 18.

Referring now to the drawings, where like elements are designated by like reference numerals, FIGS. 1 and 2 illustrate a double barrel C-Ring 10 to be introduced into the joint elbow capsule of a mammal such as a canine. FIGS. 3 and 4 illustrate an exemplary humeral implant 50 for the elbow reconstruction according to an embodiment of the present invention. FIGS. 5-13 illustrate subsequent steps of a method of elbow reconstruction according to a first embodiment of the present invention (the template embodiment). FIGS. 14-16 illustrate subsequent steps of a method of elbow reconstruction according to a second embodiment of the present invention (without a template) and employing an exemplary humeral implant 50. FIGS. 18 and 19 illustrate another exemplary humeral implant 150 for elbow reconstruction, while FIGS. 20-22 illustrate exemplary embodiments of ulnar implants 180 employed during the elbow reconstruction of the present invention. FIGS. 23-36 illustrate subsequent steps of a method of elbow reconstruction according to a third embodiment of the present invention and employing exemplary humeral implant 150 and/or ulnar implant 180.

Reference is now made to FIGS. 1 and 2, which illustrate schematic views of a double barrel C-Ring 10 that is introduced into the joint elbow capsule. Double barrel C-Ring 10 includes a drill sleeve 11 and a guide arm 13 for the humerus. Guide arm 13 preferably has the same contour as the humeral implant to be secured within the humerus, to allow sizing and positioning. Preferably, the guide arm of the double barrel C-Ring 10 is interchangeable for different sizing, if necessary.

FIGS. 3 and 4 illustrate two perspective views of a humeral implant 50 used in one of the exemplary methods of canine elbow reconstruction of the present invention, and in conjunction with the double barrel C-Ring 10 of FIGS. 1 and 2. As shown in FIGS. 3 and 4, humeral implant 50 comprises a body 52 defined by a first, articulating surface 51*a* and an opposing underside surface 51*b*, and two ends 56, 57. The articulating surface 51*a* is a smooth, continuous surface generally shaped in the form of the humeral articulating surface. The underside 51*b* is substantially flat, with at least one projection or leg extending from the underside. In an exemplary and illustrative only embodiment, and as shown in FIGS. 3 and 4, two projections or legs 54 extend from each of the ends 56, 57 of the body 52. The two legs or projections 54 extend about perpendicular to the underside 51*b*.

Through holes or openings 55 are provided within the body of each projection 54, to allow passing of at least one flexible strand (for example, at least one suture strand) therethrough. The through holes or openings 55 preferably receive a flexible strand for subsequent fixation of the implant to the bone. As shown in the drawings, openings 55 are placed about perpendicular to a longitudinal axis of the humeral implant 50. However, openings 55 may be also optimally placed in the projections 54 of the implant 50 at various angles with respect to a longitudinal axis of the humeral implant 50. In this manner, the humeral implant 50 may be employed with angularly oriented instruments, for example, to enhance the grip in more complex reconstructions, even in osteoporotic bone, and to ensure good fixation of the implant to bone.

Preferably, implant 50 is formed of cobalt-chrome alloy and all surfaces of the implant 50 (except the articulating surface 51*a*) may be coated with CP titanium plasma spray. Humeral implant 50 may be also formed of a metal such as titanium, titanium alloy, stainless steel, or other materials that possess mechanical and physical properties suitable for bone repair.

In an exemplary and illustrative embodiment only, humeral implant 50 has dimensions of about 6 by about 12 mm with an implant height of about 6 mm, and may be formed of cobalt chrome. As described above, implant 50 may be pulled in by a flexible strand such as suture, for example.

Figure 5:
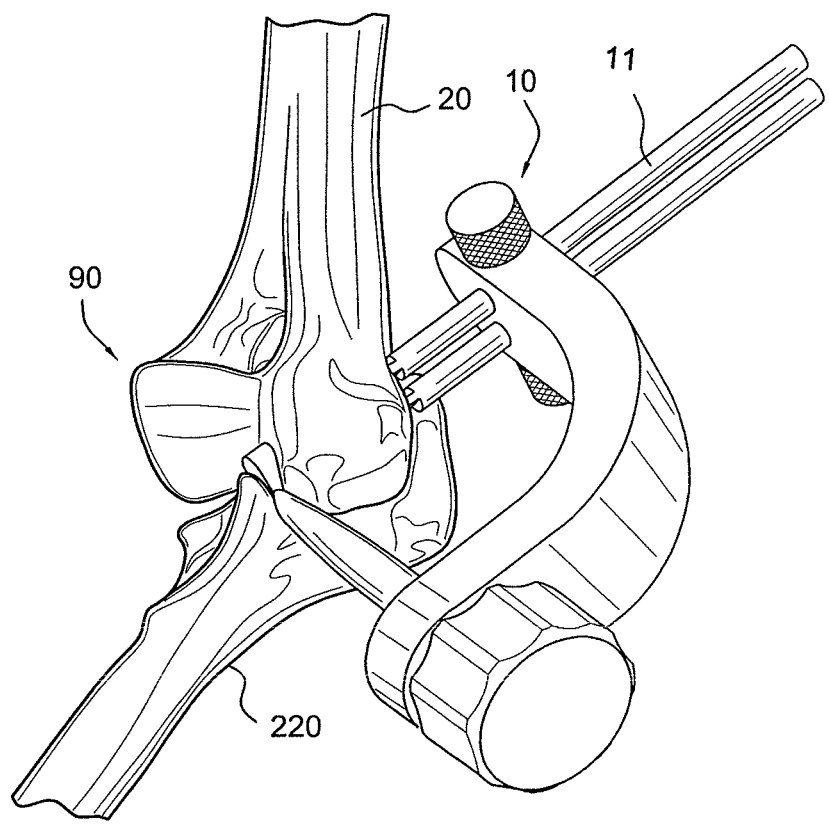
FIG. 5 illustrates a schematic view of a canine elbow undergoing a method of elbow reconstruction according to a first embodiment of the present invention.

Reference is now made to FIG. 5 which illustrates a schematic view of a mammal elbow 90 (for example, a canine elbow 90) undergoing a method of elbow reconstruction according to an embodiment of the present invention. Once the MCL is released, the double barrel C-Ring 10 (FIGS. 1 and 2) is introduced into the joint capsule. The C-Ring is introduced to size and, once the appropriate size is selected, the entire C-Ring assembly is introduced (FIG. 5). The drill sleeve 11 of the C-Ring assembly 10 is adjusted to be flush with the bone (humerus) 20.

Figure 6:
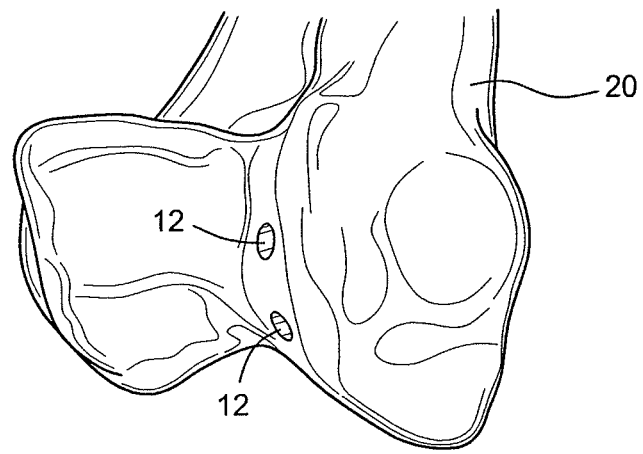
FIG. 6 illustrates a perspective view of the humerus of the elbow of FIG. 5 and at a stage of reconstruction subsequent to that shown in FIG. 5 (with two pilot holes formed within the humerus)
Figure 7:
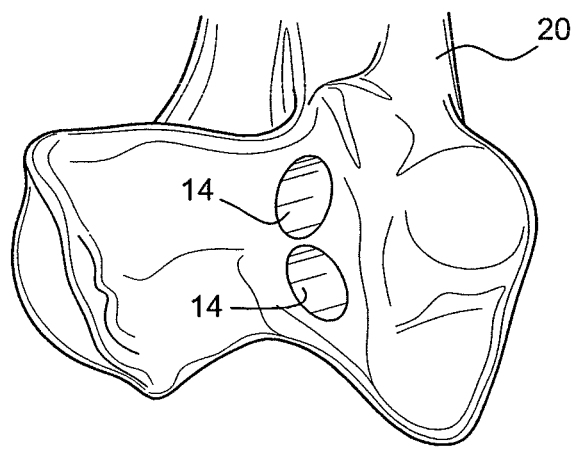
FIG. 7 illustrates another perspective view of the humerus of FIG. 5 and at a stage of reconstruction subsequent to that shown in FIG. 6 (with two sockets formed within the humerus)

Using a drill (for example, a 2.4 mm drill), two pilot holes 12 are formed in humerus 20, as shown in FIG. 6. Once the double barrel C-Ring 10 is removed, and using the two pilot holes 12, two sockets or tunnels 14 (about 6 mm deep) are created within the humerus 20 using a cutting instrument (for example, a flip retrograde cutter), as shown in FIG. 7.

In an exemplary embodiment, the sockets or tunnels 14 are formed by overdrilling the pilot holes with a cutting instrument such as a 6 mm flip cutter, which is known and described, for example, in U.S. Patent Application Publication No. 2009/0275950, the disclosure of which is incorporated by reference herein. The flip retrograde cutter disclosed in U.S. Patent Application Publication No. 2009/0275950 has a flip cutting blade that is configured to articulate between at least a first "straight" position aligned with the longitudinal axis of the cutting instrument and a second "flip" position, for example, perpendicular to the longitudinal axis of the cutting instrument. Each socket is formed by advancing the flip retrograde cutter into the elbow joint, flipping the blade into the second "flip" position, and then rotating the instrument while pulling back, to cut a socket in a retrograde manner. After drilling, the depth of each socket may be measured using a depth gage.

In an alternative and exemplary embodiment only, the sockets or tunnels may be formed in a retrograde manner, by employing a retrograde drill cutter which is inserted into the joint and threaded onto the pin tip arthroscopically in a manner similar to the insertion of the retrograde drill cutter in the technique for ACL RetroConstruction by Arthrex, Inc., Naples, Fla., as disclosed in U.S. Patent Application Publication No. 2007/0233128, the disclosure of which is incorporated in its entirety by reference herein. As described and claimed in U.S. Patent Application Publication No. 2007/0233128, the retrograde insertion technique involves threading an appropriate diameter drill cutter onto an insertion post connected to a C-Ring, inserting the mounted drill cutter into the elbow joint, and advancing the drill pin through a guide sleeve connected to the C-Ring and into the joint to engage the drill cutter. Alternatively, the sockets or tunnels may be formed in an antegrade manner.

Figure 8:
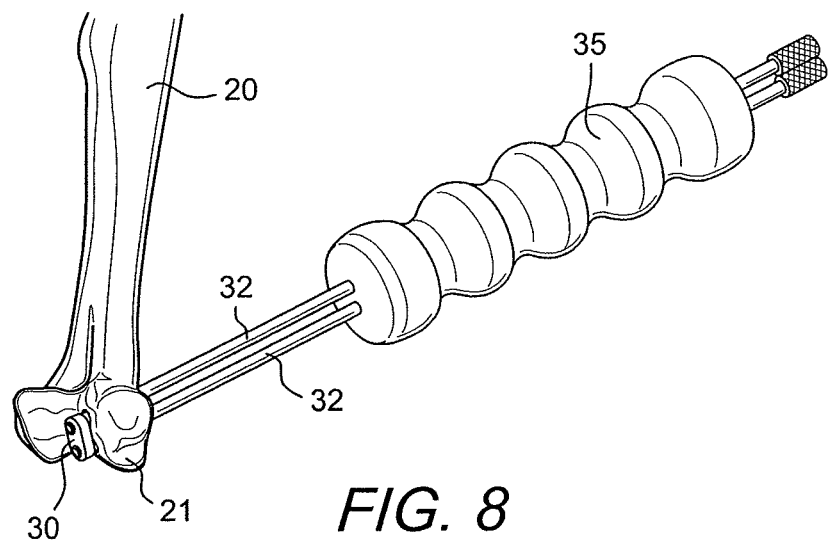
FIG. 8 illustrates a front view of the humerus of FIG. 5 and at a stage of reconstruction subsequent to that shown in FIG. 7.

Referring now to FIG. 8, a humeral assembly including a template (broach) 30, a plurality of drill pins 32 (with two thread guide posts 32), and an impact element (for example, a slap hammer) 35 is introduced over the two sockets 14. The humeral assembly is employed to create a humeral trough 40 on a curvature of a humeral condyle 21. The trough 40 may be formed either before or after the formation of the sockets.

Figure 9:
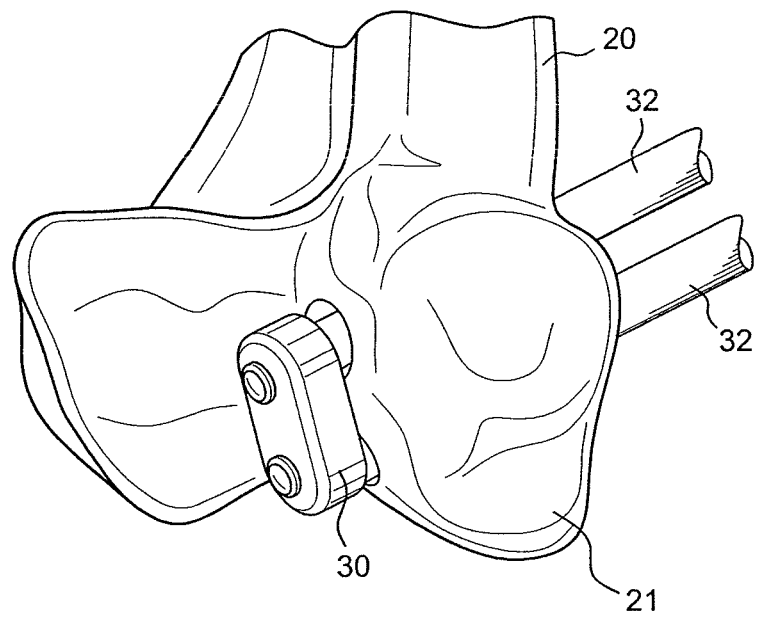
FIG. 9 illustrates a schematic view of the proximal end of the humerus of FIG. 8.
Figure 10:
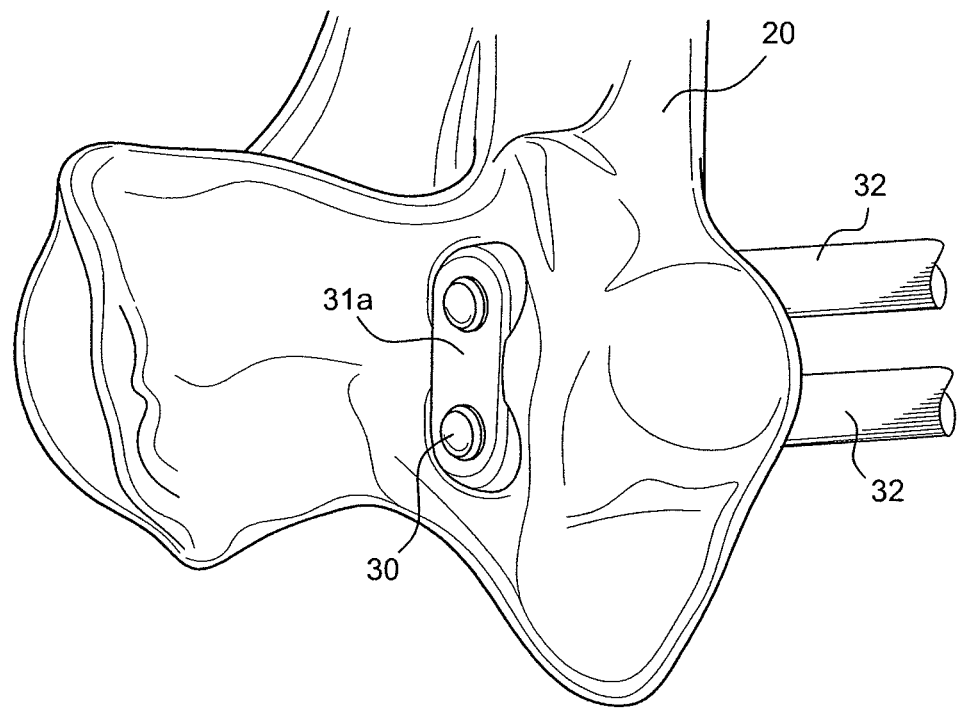
FIG. 10 illustrates a schematic view of the proximal end of the humerus of FIG. 8 and at a stage of reconstruction subsequent to that shown in FIG. 9.
Figure 11:
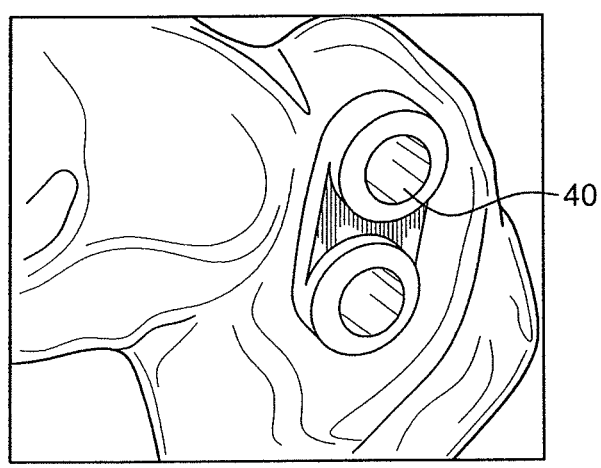
FIG. 11 illustrates another view of the proximal end of the humerus of FIG. 10.
Figure 12:
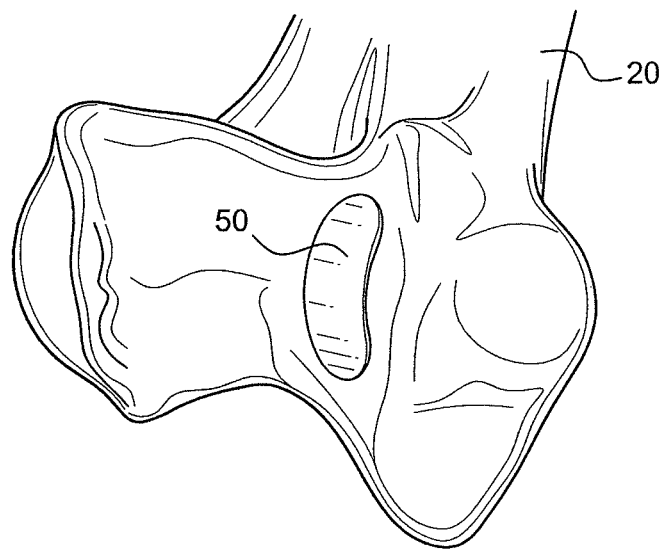
FIG. 12 illustrates a schematic view of the proximal end of the humerus of FIG. 8 and at a stage of reconstruction subsequent to that shown in FIG. 11.

The two thread guide posts 32 are introduced into the template (broach) 30, as shown in FIG. 9. Using, for example, a slap hammer 35 (FIG. 8), the template (broach) 30 is advanced into the sockets 14 until the apex of humerus 20 is flush with top surface 31*a* of the template (broach) 30, as shown in FIG. 10. By advancing the template (broach) 30 into the bone, a broached hole or trough 40 (FIG. 11) is created, which forms a hard stop or recess for insertion of the implant 50.

Once the template (broach) 30 is removed, the humeral implant 50 of FIGS. 3 and 4 is introduced over the broached contour (trough) 40 created by the removal of the template, and then the implant 50 is pulled into the trough by using sutures, for example. Cement may be injected through the holes to prepare a mantel over which the components may be placed. For additional fixation, the implant may be secured with buttons or screws. The final construct 100 is illustrated in FIG. 13.

FIGS. 14-16 illustrate steps of a method of elbow reconstruction according to a another embodiment of the present invention (i.e., an embodiment without a template). This method may be used in embodiments where the bone is hard and/or where the use of a template (broach) may be difficult. According to this exemplary embodiment, two initial sockets 60 are formed close to each other in humerus 20 (FIG. 14) to allow overlap of the socket contours (i.e., to form a snowman-shaped trough 61). According to an exemplary embodiment, the sockets may be formed as described above with reference to the formation of sockets 14 of FIG. 7.

A humeral snowman-shaped implant 80 (FIG. 15) is subsequently inserted to match the socket contour and the snowman-shaped trough 61. As in the previously-described embodiment, once the humeral implant 80 is introduced over the contour of the trough 61 created within the condyle 21 of the humerus 20, the holes or tunnels (formed during the formation of the sockets 60) may be back filled with cement to obtain a final construct 200 shown in FIG. 16.

FIGS. 17-36 illustrate implants (humeral and ulnar implants), instrumentation (humeral guide systems and drills for creation of ulnar tunnels or sockets) and methods for elbow reconstruction according to yet another exemplary embodiment of the present invention.

Figure 17:
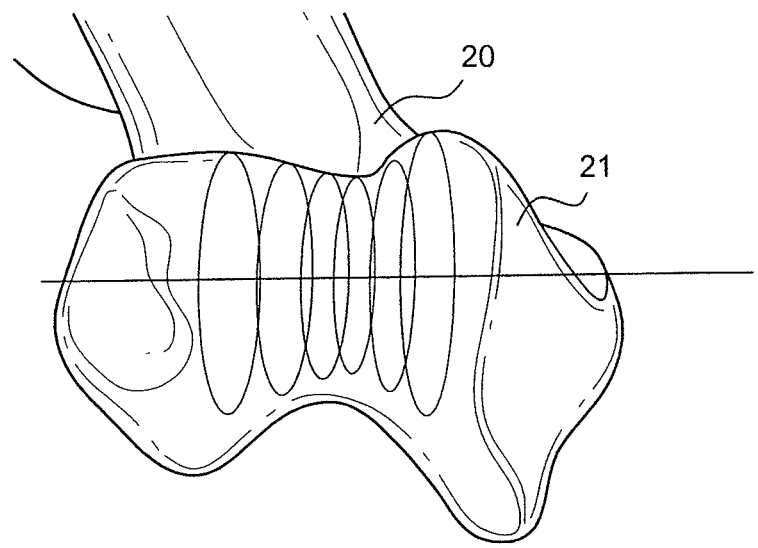
FIG. 17 illustrates a schematic view of a proximal end of a canine humerus (with the anatomical shape revolving around a center axis, with the diameter increasing from a medial side to a lateral side) and employed to determine the geometry of a humeral implant according to a third embodiment of the present invention.

FIGS. 18 and 19 illustrate an exemplary embodiment of humeral implant 150 of the present invention provided with a simple or compound curvature, which follows the anatomic geometry of the condyle 21 of humerus 20 of FIG. 17. Humeral implant 150 comprises a body 152 defined by a first, articulating surface 151a and an opposing underside surface 151b. The articulating surface 151a is generally shaped in the form of the humeral articulating surface. The underside 151b is substantially flat.

Preferably, implant 150 is formed of cobalt-chrome alloy and all surfaces of the implant 150 (except the articulating surface 151a) may be coated with CP titanium plasma spray. Humeral implant 150 may be also formed of a metal such as titanium, titanium alloy, stainless steel, or other materials that possess mechanical and physical properties suitable for bone repair. In an exemplary and illustrative embodiment only, humeral implant 150 has dimensions of about 6 by about 10.5 mm with an implant height of about 6 mm, and may be formed of cobalt chrome. Implant 150 may be provided in various sizes (for example, small, medium or large) and may be press fit. In yet another exemplary embodiment, body 152 of implant 150 may be formed of different materials 152a (for the articulating region) and 152b (for the underside region).

FIGS. 20-22 illustrate ulnar implants 180a, 180b, 180c having different contours (i.e., a concave, angled and flat, respectively) and formed of a biocompatible material such as UHMWPE, for example. Ulnar implants 180a, 180b, 180c may be provided with a threaded region 185a, 185b, 185c adjacent to a substantially cylindrical region 186a, 186b, 186c.

Figure 23:
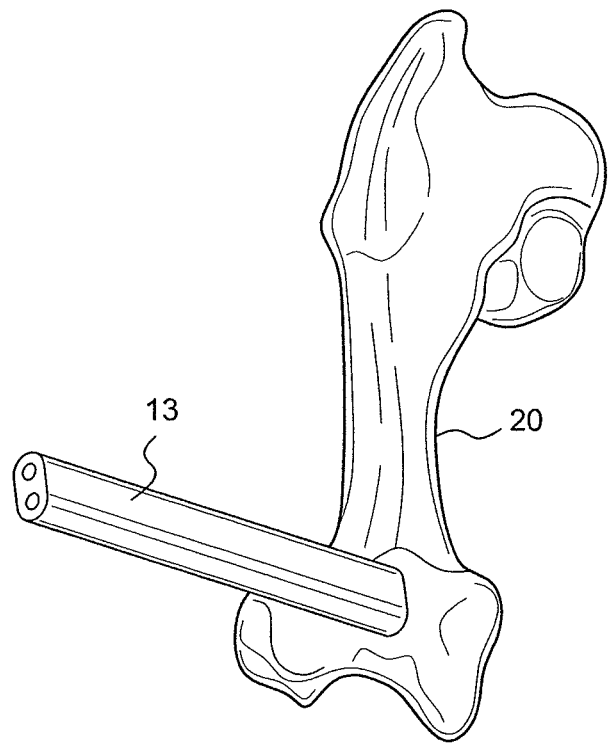
FIG. 23 illustrates a schematic view of a humerus of a canine elbow undergoing a method of elbow reconstruction according to a third embodiment of the present invention.
Figure 24:
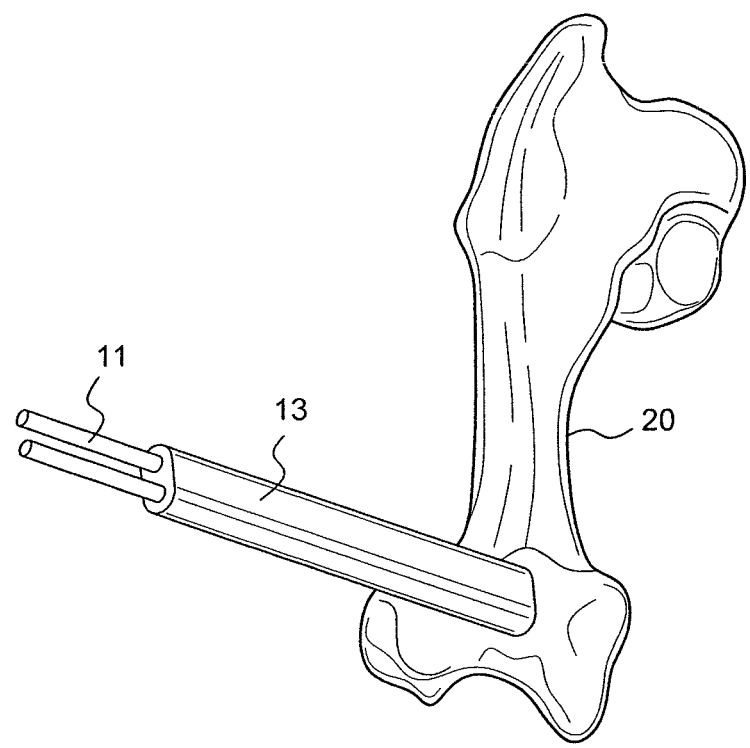
FIG. 24 illustrates a schematic view of the humerus of FIG. 23 and at a stage of reconstruction subsequent to that shown in FIG. 23.
Figure 25:
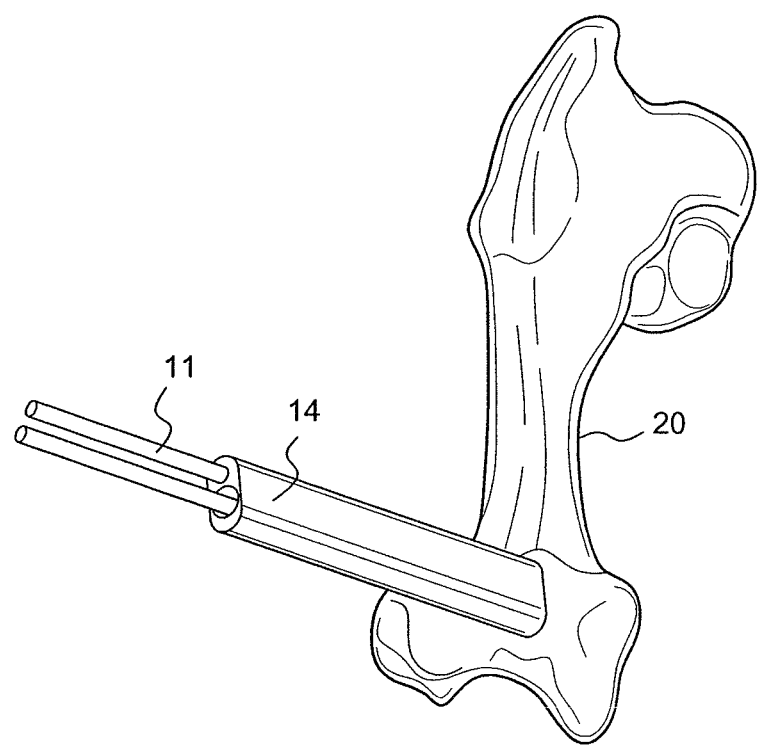
FIG. 25 illustrates a schematic view of the humerus of FIG. 23 and at a stage of reconstruction subsequent to that shown in FIG. 24.

FIGS. 23-32 illustrate various components of a humeral guide system of the present invention employed for the elbow reconstruction of the present invention. Guide 13 is positioned on the condyle 21 to determine alignment, as shown in FIG. 23. The guide is cannulated for two drill pins 11 (for example, for two 2.4 mm drill pins) shown in FIG. 24. Once the two drill pins 11 are inserted, the guide is removed. FIG. 25 illustrates the insertion of second drill depth stop guide 14. This guide allows accurate depth stop for subsequent creation of holes or sockets for the implant.

Figure 26:
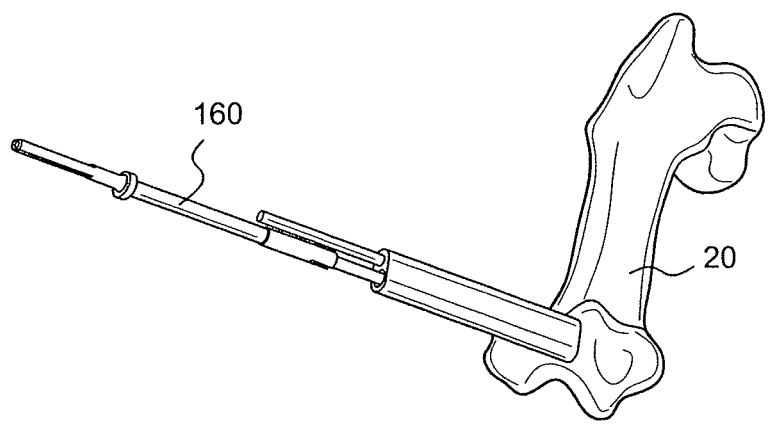
FIG. 26 illustrates a schematic view of the humerus of FIG. 23 and at a stage of reconstruction subsequent to that shown in FIG. 25.
Figure 27:
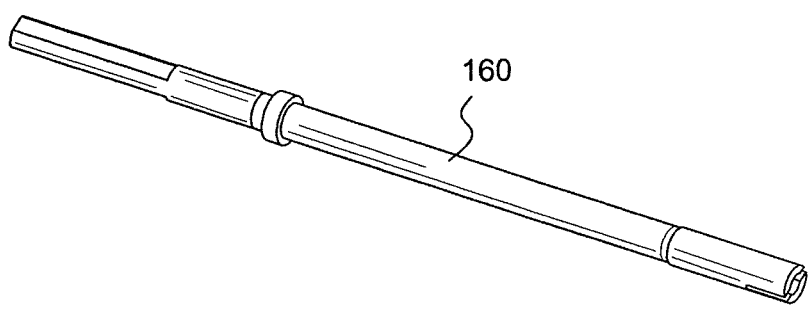
FIG. 27 illustrates a perspective view of an exemplary drill with shoulder used to create a socket within the proximal end of the humerus of FIG. 26.
Figure 28:
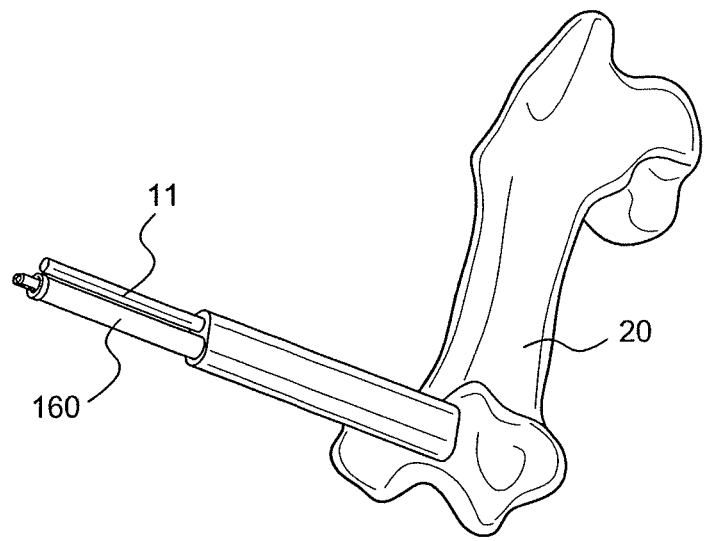
FIG. 28 illustrates a schematic view of the humerus of FIG. 23 and at a stage of reconstruction subsequent to that shown in FIG. 26.
Figure 29:
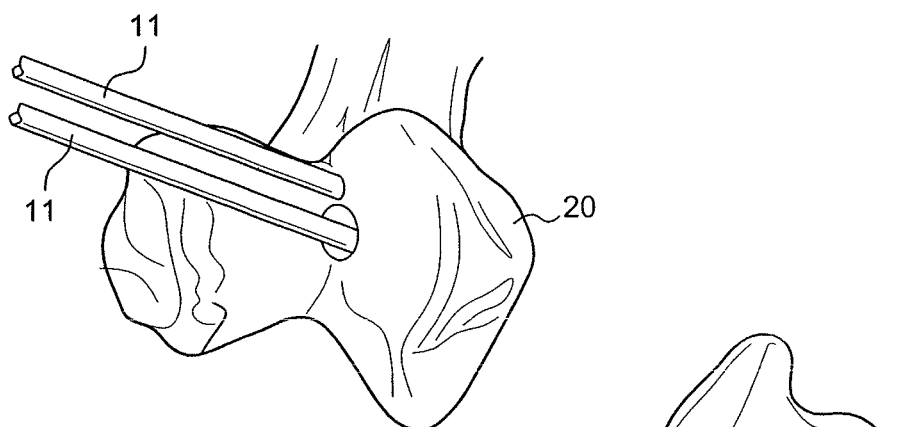
FIG. 29 illustrates a schematic view of the humerus of FIG. 23 and at a stage of reconstruction subsequent to that shown in FIG. 28.
Figure 30:
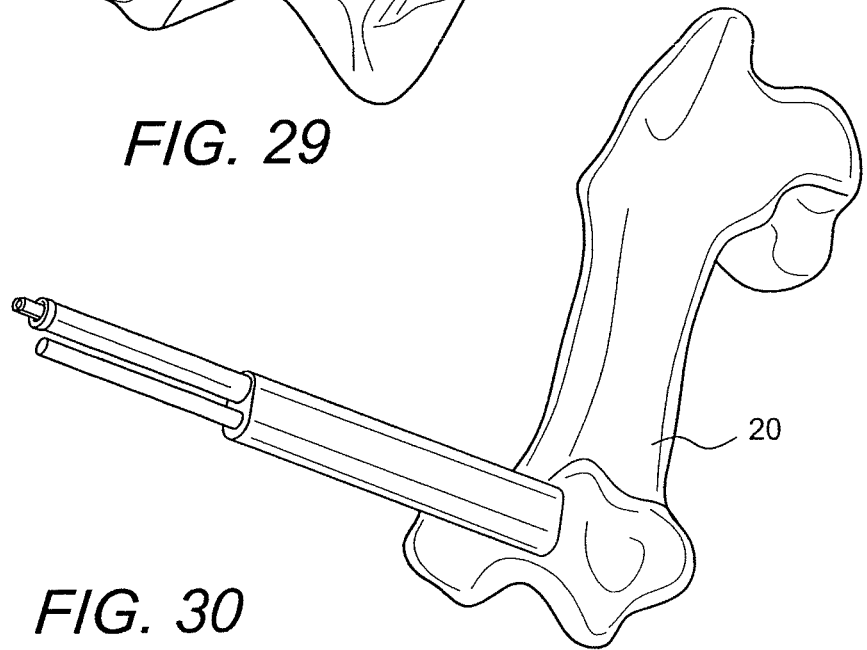
FIG. 30 illustrates a schematic view of the humerus of FIG. 23 and at a stage of reconstruction subsequent to that shown in FIG. 29.

A drill with shoulder 160 (for example, a 6 mm drill with shoulder) is introduced to create a first socket 114 (for example, a 6 mm socket with a 6 mm drill with shoulder), as shown in FIGS. 26 and 27. Drill hard stops when shoulder of drill contacts depth stop sleeve (FIG. 28). The 2.4 mm drill pins are left and the depth stop sleeve is removed, as shown in FIG. 29. The depth stop sleeve is flipped and then the drilling for the other side (for the other hole or socket 114) is repeated (FIG. 30). The second socket or hole 114 is formed (for example, a 6 mm socket with a 6 mm drill with shoulder).

Figure 31:
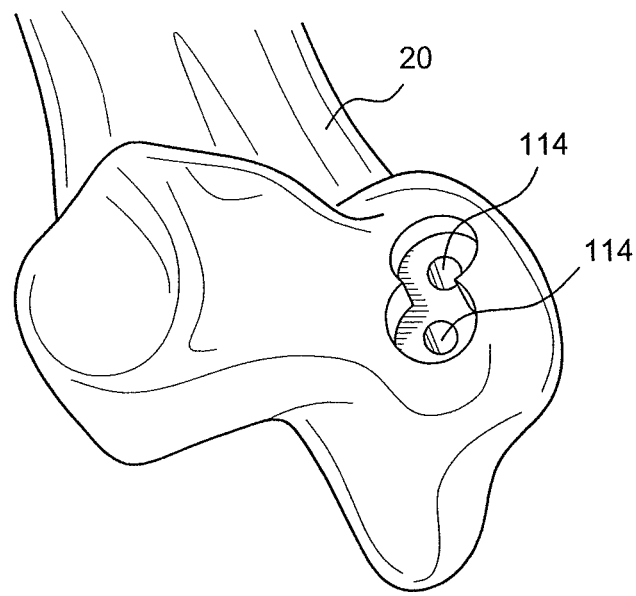
FIG. 31 illustrates a schematic view of the humerus of FIG. 23 and at a stage of reconstruction subsequent to that shown in FIG. 30.
Figure 32:
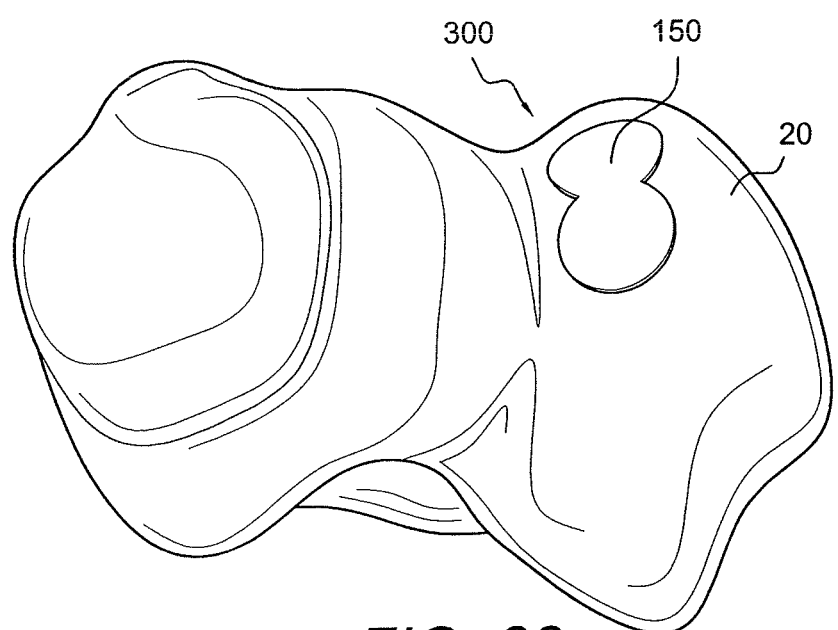
FIG. 32 illustrates a schematic view of the humerus of FIG. 23 and at a stage of reconstruction subsequent to that shown in FIG. 26.

FIG. 31 illustrates holes or sockets 114 formed within humerus 20 with a cutting instrument (for example, a cutting instrument as described above for the formation of holes or sockets 14 of FIG. 7). Holes or sockets 114 are created to accommodate humeral implant 150 which is inserted within the sockets as shown in FIG. 32. The implant is pressed within the prepared sockets.

Figure 33:
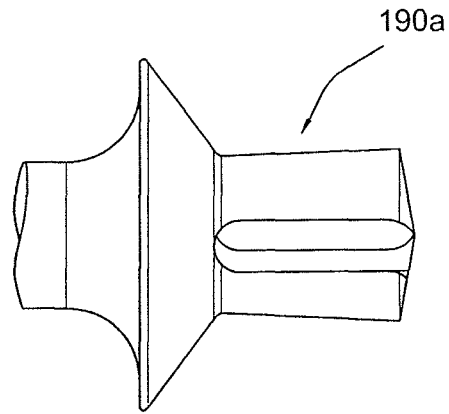
FIG. 33 illustrates a schematic view of a drill with hard stop according to a first embodiment and used to create an ulnar tunnel.
Figure 34:
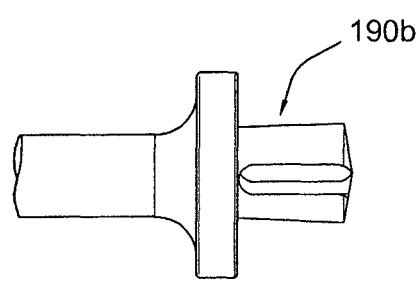
FIG. 34 illustrates a schematic view of a drill with hard stop according to a second embodiment and used to create an ulnar tunnel.
Figure 35:
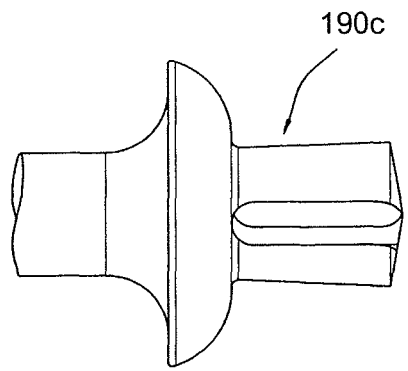
FIG. 35 illustrates a schematic view of a drill with hard stop according to a third embodiment and used to create an ulnar tunnel.

FIGS. 33-35 illustrate three drills with hard stops 190a, 190b, 190c employed for the formation of an ulnar tunnel or socket (to accommodate, for example, an ulnar implant such as ulnar implant 180a, 18ab, 180c provided with different contours (i.e., a concave, angled and flat, respectively) and shown in FIGS. 20-22). The depth is preferably a positive stop on ulna articulating surface.

Figure 36:
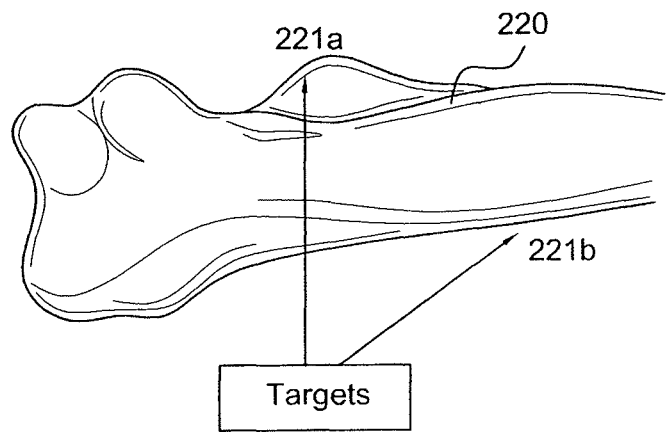
FIG. 36 illustrates a schematic view of a canine ulna showing targets for positioning ACL C-ring during a method of canine elbow reconstruction of the present invention.

FIG. 36 illustrates ulna 220 (also shown in FIG. 5) prepared for ulnar tunnel formation. In an exemplary embodiment, a 2.4 mm guide drill is drilled through the previously-created 2.4 mm hole pins in the humerus 20, to obtain alignment with ulna 220. Alternatively, an ACL C-ring may be employed to target the ridge and surface of ulna 220 (as shown by targets 221a and 221b of FIG. 36).

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. An elbow repair assembly, comprising:
   a template configured to be aligned to a curvature of a humeral condyle and to assist in the formation of a humeral trough within the humeral condyle for an elbow repair;
   two drill pins with two thread guide posts, the two thread guide posts being introduced into the template to assist in the formation of the humeral trough;
   a retrograde cutter for removing bone from the humeral condyle to form the trough; and
   a humeral implant having an outer, articulating surface shaped in the form of the humeral condyle and an opposing underside surface which is substantially flat, and two projections extending from the underside surface opposite the outer, articulating surface and in a direction about perpendicular to the outer, articulating surface, for securing the humeral implant in the humeral trough formed with the template and the two drill pins with two thread guide posts, wherein each of the projections comprises a through hole for receiving at least one flexible strand, the humeral implant being pulled into the humeral trough by using the at least one flexible strand passing through the projections.

2. The elbow repair assembly of claim 1, wherein the at cutter is a retrograde flip cutter.

3. The elbow repair assembly of claim 1, wherein the humeral implant is formed of cobalt chrome or cobalt chrome alloy.

4. The elbow repair assembly of claim 1, wherein the humeral condyle is a canine humeral condyle.

* * * * *